(12) United States Patent
Fischer et al.

(10) Patent No.: US 8,486,995 B2
(45) Date of Patent: Jul. 16, 2013

(54) ACARICIDAL ACTIVE SUBSTANCE COMBINATIONS

(75) Inventors: Reiner Fischer, Monheim (DE);
Emmanuel Salmon, Köln (DE); Heike Hungenberg, Langenfeld (DE);
Jingquan Guo, Beijing (CN)

(73) Assignee: Bayer Corporation, Monheim (DE)

( * ) Notice: Subject to any disclaimer, the term of this patent is extended or adjusted under 35 U.S.C. 154(b) by 596 days.

(21) Appl. No.: 12/664,977

(22) PCT Filed: Jun. 27, 2008

(86) PCT No.: PCT/EP2008/005268
§ 371 (c)(1),
(2), (4) Date: Mar. 12, 2010

(87) PCT Pub. No.: WO2009/003649
PCT Pub. Date: Jan. 8, 2009

(65) Prior Publication Data
US 2010/0216738 A1    Aug. 26, 2010

(30) Foreign Application Priority Data

Jun. 29, 2007  (EP) .................................... 07111412
Dec. 21, 2007  (CN) ......................... 2007 1 0307617

(51) Int. Cl.
*A01N 43/12*      (2006.01)
*A01N 43/26*      (2006.01)
*A01N 43/30*      (2006.01)
*A61K 31/34*      (2006.01)
*A61K 31/335*     (2006.01)
*A61K 31/36*      (2006.01)

(52) U.S. Cl.
USPC .......................................... 514/462; 514/465

(58) Field of Classification Search
None
See application file for complete search history.

(56) References Cited

U.S. PATENT DOCUMENTS

| | | | |
|---|---|---|---|
| 3,272,854 A | 9/1966 | Covey et al. | |
| 3,835,176 A | 9/1974 | Matsuo et al. | |
| 4,310,519 A | 1/1982 | Albers-Schonberg et al. | |
| 5,262,383 A | 11/1993 | Fischer et al. | |
| 6,576,661 B1 | 6/2003 | Brück et al. | |
| 6,716,874 B1 | 4/2004 | Bretschneider et al. | |
| 6,818,670 B2 * | 11/2004 | Bruck et al. | 514/473 |
| 8,101,656 B2 * | 1/2012 | Fischer et al. | 514/462 |
| 2005/0187215 A1 | 8/2005 | Fischer et al. | |
| 2007/0015825 A1 | 1/2007 | Fischer et al. | |
| 2010/0056620 A1 | 3/2010 | Fischer et al. | |
| 2010/0173987 A1 | 7/2010 | Fischer et al. | |

FOREIGN PATENT DOCUMENTS

| | | |
|---|---|---|
| CA | 1098063 A1 | 3/1981 |
| DE | 27 17 040 A1 | 11/1977 |
| DE | 199 39 395 A1 | 4/2000 |
| EP | 0 089 202 A1 | 9/1983 |
| EP | 0 134 439 A1 | 3/1985 |
| EP | 0 234 045 A2 | 2/1987 |
| EP | 0 326 329 A2 | 2/1989 |
| WO | WO 93/10083 | 5/1993 |
| WO | WO 01/33966 A2 | 5/2001 |
| WO | WO 2005/004605 A1 | 1/2005 |
| ZA | 99/06662 | 10/2000 |

OTHER PUBLICATIONS

Bauer, T.A., et al., "Response of Selected Weed Species to Postemergence Imazethapyr and Benazon," *Weed Tech.* 9:236-242, The Weed Science Society of America, United States (1995).
Blackshaw, R.E., "HOE-39866 Use in Chemical Fallow Systems," *Weed Tech.* 3:420-428, The Weed Science Society of America, United States (1989).
Blackshaw, R.E., "Synergistic Mixes of DPX-A7881 and Clopyralid in Canola (*Brassica napus*),"*Weed Tech.* 3:690-695, The Weed Science Society of America, United States (1989).
Blackshaw, R.E., et al., "Herbicide Combinations for Postemergent Weed Control in Safflower (*Carthamus tinctorius*)," *Weed Tech.* 4:97-104, The Weed Science Society of America, United States (1990).
Blouin, D.C., et al., "Analysis of Synergistic and Antagonistic Effects of Herbicides Using Nonlinear Mixed-Model Methodology," *Weed Tech.* 18:464-472, The Weed Science Society of America, United States (2004).
Bradley, P.R., et al., "Response of Sorghum (*Sorghum bicolor*) to Atrazine, Ammonium Sulfate, and Glyphosate," *Weed Tech.* 14:15-18, The Weed Science Society of America, United States (2000).
Buker, III, R.S., et al., "Confirmation and Control of a Paraquat-Tolerant Goosegrass (*Eleusine indica*) Biotype," *Weed Tech.* 16:309-313, The Weed Science Society of America, United States (2002).
Burke, I.C., et al., "CGA-362622 Antagonizes Annual Grass Control with Clethodim," *Weed Tech.* 16:749-754, The Weed Science Society of America, United States (2002).
Colby, S.R., "Calculating Synergistic and Antagonistic Responses of Herbicide Combinations," *Weeds*, 15:20-22, Weed Science Society of America, United States (1967).

(Continued)

*Primary Examiner* — Lawrence E Crane
(74) *Attorney, Agent, or Firm* — Sterne, Kessler, Goldstein & Fox P.L.L.C.

(57) ABSTRACT

Disclosed is a method of controlling insects or acarids comprising contacting crops or their environment with a compound of the formula (I):

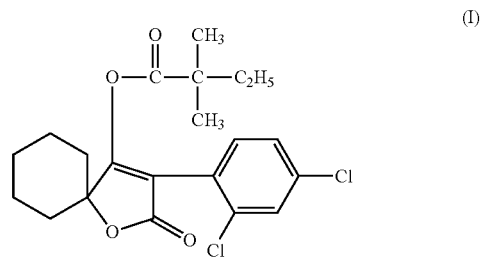

and least one compound selected from the group consisting of: bifenazate, fenpyroximate pyridaben, fenazaquin, abamectin, emamectin benzoate, fenpropathrin and propargite.

8 Claims, No Drawings

OTHER PUBLICATIONS

Flint, J.L., et al., "Analyzing Herbicide Interactions, A Statistical Treatment of Colby's Method," *Weed Tech.* 2:304-309, The Weed Science Society of America, United States (1988).

Gillespie, G.R., and Nalewaja, J.D., "Wheat (*Triticum aestivum*) Response to Triallate Plus Chlorsulfuron," *Weed Tech.* 3:20-23, The Weed Science Society of America, United States (1989).

Green, J.M., et al., "Metribuzin and Chlorimuron Mixtures for Preemergence Broadleaf Weed Control in Soybeans, *Glycine max*," *Weed Tech.* 2:355-363, The Weed Science Society of America, United States (1988).

Harker, N.K., and O'Sullivan, P.A., "Synergistic Mixtures of Sethoxydim and Fluazifop on Annual Grass Weeds," *Weed Tech.* 5:310-316, The Weed Science Society of America, United States (1991).

Kent, L.M., et al., "Effect of Ammonium Sulfate, Imazapyr, and Environment on the Phytotoxicity of Imazethapyr," *Weed Tech.* 5:202-205, The Weed Science Society of America, United States (1991).

Kotoula-Syka, E., et al., "Interactions between SAN 582H and Selected Safeners on Grain Sorghum (*Sorghum bicolor*) and Corn (*Zea Mays*)," *Weed Tech.* 10:299-304, The Weed Science Society of America, United States (1996).

Lanclos, D.Y., et al., "Glufosinate Tank-Mix Combinations in Glufosinate-Resistant Rice (*Oryza sativa*)," *Weed Tech.* 16:659-663, The Weed Science Society of America, United States (2002).

Norris, J.L., et al., "Weed Control from Herbicide Combinations with Three Formulations of Glyphosate," *Weed Tech.* 15:552-558, The Weed Science Society of America, United States (2001).

Novosel, K.M., et al., "Metolachlor Efficacy as Influenced by Three Acetolactate Synthase-Inhibiting Herbicides," *Weed Tech.* 12:248-253, The Weed Science Society of America, United States (1998).

Palmer, E.W., et al., "Broadleaf Weed Control in Soybean (*Glycine max*) with CGA-277476 and Four Postemergence Herbicides," *Weed Tech.* 14:617-623, The Weed Science Society of America, United States (2000).

Rummens, F.H.A., "An Improved Definition of Synergistic and Antagonistic Effects," *Weed Science* 23(1):4-6, The Weed Science Society of America, United States (1975).

Salzman, F.P., and Renner, K.A., "Response of Soybean to Combinations of Clomazone, Metribuzin, Linuron, Alachlor, and Atrazine," *Weed Tech.* 6:922-929, The Weed Science society of America, United States (1992).

Scott, R.C., et al., "Spray Adjuvant, Formulation, and Environmental Effects on Synergism from Post-Applied Tank Mixtures of SAN 582H with Fluazifop-P, Imazethapyr, and Sethoxydim," *Weed Tech.* 12:463-469, The Weed Science Society of America, United States (1998).

Shaw, D.R. and Arnold, J.C., "Weed Control from Herbicide Combinations with Glyphosate," *Weed Tech.* 16:1-6, The Weed Science Society of America, United States (2002).

Snipes, C.E., and Allen, R.L., "Interaction of Graminicides Applied in Combination with Pyrithiobac," *Weed Tech.* 10:889-892, The Weed Science Society of America, United States (1996).

Sun, Y.-P. & Johnson, E.R., "Analysis of Joint Action of Insecticides against House Flies", *J. Econ. Entomol.*, 53:887-892, Journal of Economic Entomology, United States (1960).

Thiel, M. & Nauen, R., "Untersuchungen zur Akaridresistenz an Populationen der Obstbaumspinnmilbe, *Panonychus ulmi* KOCH (Acari:Tetranychidae aus dem Bodenseegebiet)," *Gesunde Pflanzen*58:239-245, Springer-Verlag, Germany (2006).

Wachendorff, U. et al., "The biological profile of spirodiclofen (Envidor)—A new selective tetronic acid acaricide," Pflanzenschutz-Nachrichten Bayer 55/2002,2-3, 149-176, Germany (2002).

Wehtje, G. and Walker, R.H., "Interaction of Glyphosate and 2,4-DB for the Control of Selected Morningglory (*Ipomoea* spp.) Species," *Weed Tech.* 11:152-156, The Weed Science Society of America, United States (1997).

Zhang, W., et al., "Fenoxaprop Interactions for Barnyardgrass (*Echinochloa crus-galli*) Control in Rice," *Weed Tech.* 19:293-297, The Weed Science Society of America, United States (2005).

English Translation of the Written Opinion of the International Searching Authority for International Application No. PCT/EP2008/005268, European Patent Office, Netherlands, mailed on Jan. 19, 2010.

International Search Report for International Application No. PCT/EP2008/005268, European Patent Office, Netherlands, mailed on Aug. 12, 2009.

Office Action mailed Aug. 14, 2003, in U.S. Appl. No. 10/412,492 (now U.S. Patent No. 6,818,670), inventors Brick et al., filed Apr. 11, 2003.

Office Action mailed May 18, 2004, in U.S. Appl. No. 10/412,492 (now U.S. Patent No. 6,818,670), inventors Bruck et al., filed Apr. 11, 2003.

Office Action mailed Sep. 2, 2009, in U.S. Appl. No. 10/563,803 (now U.S. Patent No. 8,101,656), inventors Fischer et al., filed Jun. 28, 2006.

Office Action mailed Apr. 15, 2010, in U.S. Appl. No. 10/563,803 (now U.S. Patent No. 8,101,656), inventors Fischer et al., filed Jun. 28, 2006.

Office Action mailed Feb. 9, 2011, in U.S. Appl. No. 10/563,803 (now U.S. Patent No. 8,101,656), inventors Fischer at al., filed Jun. 28, 2006.

Office Action mailed Jan. 31, 2012, in co-pending U.S. Appl. No. 12/304,958, inventors Fischer et al., filed Aug. 26, 2009.

* cited by examiner

ACARICIDAL ACTIVE SUBSTANCE COMBINATIONS

The present invention relates to the use of active substance combinations which consist firstly of a known dihydrofuranone derivative and secondly of further known pesticidal active substances, which active substance combinations are used for controlling animal pests, in particular for controlling animal pests from the order of the mites.

It has already been disclosed that the dihydrofuranone derivative of the formula

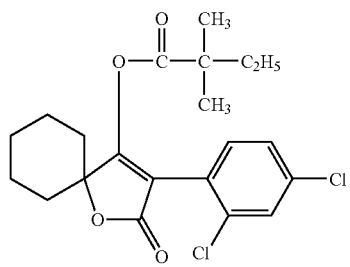
(I)

can be employed for controlling animal pests such as insects and undesirable acarids (cf. EP-A-0528156). While the activity of the substance is good, it leaves something to be desired in some cases when used at low application rates.

Mixtures of (I) with other insecticides and/or acaricides are also known: DE-A-19939395, WO 00/56156, WO 01/24634 and WO 01/33966.

It has now been found that the active substance combinations comprising the dihydrofuranone derivative of the formula

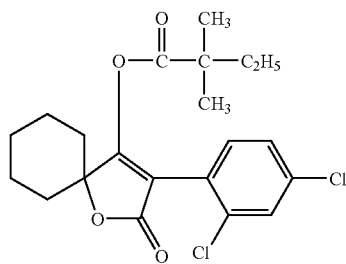
(I)

and active substances from the IRAC classes of the sodium channel modulators/blockers and/or site I electron transport inhibitors and/or chloride channel activators and/or inhibitors of the magnesium-stimulated ATPase and/or bifenazate are particularly suitable for controlling animal pests, in particular from the order of the mites, in annual or perennial crops. Surprisingly, the acaricidal activity of the active substance combinations, in particular, is greater than the sum of the activities of the individual active substances.

Especially preferred are the active substance combinations comprising the compound of the formula (I) and at least one of the following compounds:

(1) the phenyl hydrazine derivative of the formula

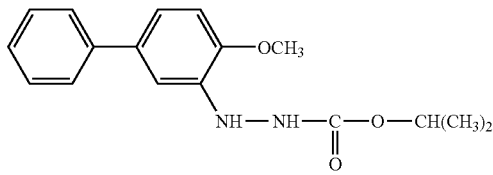
(II)

bifenazate, disclosed in WO 93/10 083,
and/or (2) from the class of the site (I) electron transport inhibitors, the pyrazole derivative of the formula

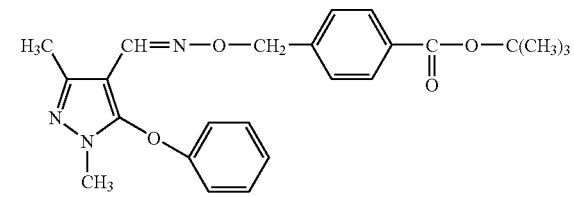
(III)

fenpyroximate, disclosed in EP-A-234 045,
and/or the pyridazinone derivative of the formula

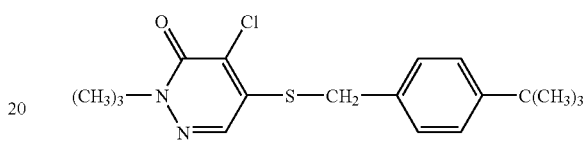
(IV)

pyridaben, disclosed in EP-A-134 439,
and/or
fenazaquin

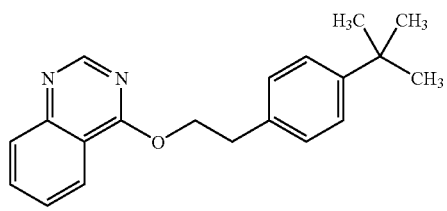
(IV)

disclosed in EP-A-326 329,
and/or (3) from the class of the chloride channel activators
abamectin (VI), disclosed in DE-A-02717040,
and/or
emamectin benzoate (VII), disclosed in EP-A-0089202,
and/or (4) from the class of the sodium channel modulators/blockers

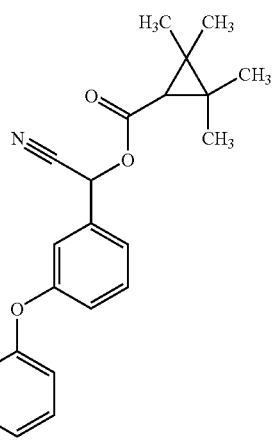
(VIII)

fenpropathrin, disclosed in DE-A-02231312,
and/or (5) from the class of the magnesium-stimulated ATPase active substances

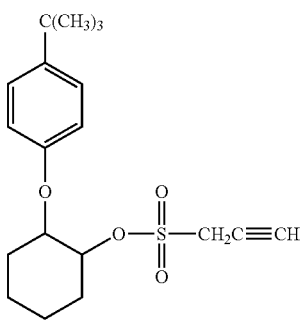
(IX)

propargite, disclosed in U.S. Pat. No. 3,272,854.

Besides the active substance of formula (I), the active substance combinations comprise at least one active substance from the compounds of the formulae (II) to (IX).

In addition, the active substance combinations may also comprise further fungicidally, acaracidally or insecticidally active admixture components.

When the active substances are present in certain weight ratios in the active substance combinations according to the invention, the improved activity is particularly pronounced. However, the weight ratios of the active substances in the active substance combinations can be varied within a relatively wide range. In general, the combinations according to the invention comprise the active substance of the formula (I) and the mixing partner in the preferred and especially preferred mixing ratios detailed in the table hereinbelow:

the mixing ratios are based on weight ratios. The ratio is to be understood as meaning active substance of the formula (I): mixing partner

| Mixing partner | Preferred mixing ratio | Especially preferred mixing ratio |
|---|---|---|
| Bifenazate (II) | 5:1 to 1:25 | 5:1 to 1:5 |
| Fenpyroximate (III) | 25:1 to 1:25 | 5:1 to 1:5 |
| Pyridaben (IV) | 25:1 to 1:25 | 5:1 to 1:5 |
| Fenazaquin (V) | 25:1 to 1:25 | 5:1 to 1:5 |
| Abamectin (VI) | 125:1 to 1:25 | 25:1 to 1:5 |
| Emamectin benzoate (VII) | 125:1 to 1:25 | 5:1 to 1:5 |
| Fenpropathrin (VIII) | 25:1 to 1:25 | 5:1 to 1:5 |
| Propargite (IX) | 10:1 to 1:25 | 5:1 to 1:5 |

The active substance combinations are suitable for controlling animal pests, preferably arthropods and nematodes, in particular insects and/or arachnids, which are found in viticulture and fruit production, in horticulture, in agriculture and in forests. They are active against normally-sensitive and resistant species and against all or some developmental stages. The abovementioned pests include:

From the order of the Isopoda, for example *Oniscus asellus, Armadillidium vulgare, Porcellio scaber.*

From the order of Diplopoda, for example *Blaniulus guttulatus.*

From the order of Chilopoda, for example *Geophilus carpophagus, Scutigera* spp.

From the order of Symphyla, for example *Scutigerella immaculata.*

From the order of Thysanura, for example *Lepisma saccharina.*

From the order of Collembola, for example *Onychiurus armatus.*

From the order of Orthoptera, for example *Acheta domesticus, Gryllotalpa* spp., *Locusta migratoria migratorioides, Melanoplus* spp., *Schistocerca gregaria.*

From the order of Blattaria, for example *Blatta orientalis, Periplaneta americana, Leucophaea maderae, Blattella germanica.*

From the order of Dermaptera, for example *Forficula auricularia.*

From the order of Isoptera, for example *Reticulitermes* spp.

From the order of Phthiraptera, for example *Pediculus humanus corporis, Haematopinus* spp., *Linognathus* spp., *Trichodectes* spp., *Damalinia* spp.

From the order of Thysanoptera, for example *Hercinothrips femoralis, Thrips tabaci, Thrips palmi,* Frankliniella accidentalis.

From the order of Heteroptera, for example *Eurygaster* spp., *Dysdercus intermedius, Piesma quadrata, Cimex lectularius, Rhodnius prolixus, Triatoma* spp.

From the order of Homoptera, for example *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order of Lepidoptera, for example *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus.*

From the order of Hymenoptera, for example *Diprion* spp., *Hoplocampa* spp., *Lasius* spp., *Monomorium pharaonis, Vespa* spp.

From the order of Diptera, for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of Siphonaptera, for example *Xenopsylla cheopis, Ceratophyllus* spp.

From the class of the Arachnida, for example *Scorpio maurus, Latrodectus mactans, Acarus siro, Argas* spp., *Aculus* spp., *Ornithodoros* spp., *Dermanyssus gallinae, Eriophyes* spp., *Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Eotetranychus* spp., *Oligonychus* spp., *Hemitarsonemus* spp., *Brevipalpus* spp. in annual crops such as, for example, vegetables, melons, ornamentals, maize, but also in perennial plants such as, for example, citrus, pome fruit and stone fruit, spices, conifers and other ornamentals, and in afforestations.

The crops to be protected which have only been described in general terms will be described in greater detail and specified hereinbelow. Thus, as regards the use, vegetables are understood as meaning for example fruiting vegetables and inflorescences as vegetables, for example bell peppers, chilies, tomatoes, aubergines, cucumbers, pumpkins, courgettes, broad beans, climbing and dwarf beans, peas, artichokes; but also leafy vegetables, for example head-forming lettuce, chicory, endives, various types of cress, of rocket, lamb's lettuce, iceberg lettuce, leeks, spinach, Swiss chard;

furthermore tuber vegetables, root vegetables and stem vegetables, for example celeriac/celery, beetroot, carrots, radish, horseradish, scorzonera, asparagus, beet for human consumption, palm hearts, bamboo shoots, furthermore bulb vegetables, for example onions, leeks, Florence fennel, garlic;

furthermore *Brassica* vegetables such as cauliflower, broccoli, kohlrabi, red cabbage, white cabbage, curly kale, Savoy cabbage, Brussels sprouts, Chinese cabbage.

Regarding the use, perennial crops are understood as meaning citrus, such as, for example, oranges, grapefruits, tangerines, lemons, limes, Seville oranges, kumquats, satsumas;

but also pome fruit such as, for example, apples, pears and quinces, and stone fruit, such as, for example, peaches, nectarines, cherries, plums, quetsch, apricots;

furthermore grapevines, hops, olives, tea and tropical crops such as, for example, mangoes, papayas, figs, pineapples, dates, bananas, durians, kaki fruit, coconuts, cacao, coffee, avocados, lychees, maracujas, guavas, moreover almonds and nuts such as, for example, hazelnuts, walnuts, pistachios, cashew nuts, para nuts, pecan nuts, butternuts, chestnuts, hickory nuts, macadamia nuts, peanuts, moreover also soft fruit such as, for example, currants, gooseberries, raspberries, blackberries, blueberries, strawberries, cranberries, including American cranberries, kiwi fruit.

As regards the use, ornamentals are understood as meaning annual and perennial plants, for example cut flowers such as, for example, roses, carnations, gerbera, lilies, marguerites, chrysanthemums, tulips, narcissus, anemones, poppies, amaryllis, dahlias, azaleas, hibiscus, but also for example bedding plants, pot plants and perennials such as, for example, roses, Tagetes, violas, geraniums, fuchsias, hibiscus, chrysanthemum, busy lizzie, cyclamen, African violet, sunflowers, begonias, furthermore for example bushes and conifers such as, for example, ficus, rhododendron, firs, spruces, pines, including umbrella pines, yews, juniper, oleander.

As regards the use, spices are understood as meaning annual and perennial plants such as, for example, aniseed, chili pepper, paprika, pepper, vanilla, marjoram, thyme, cloves, juniper berries, cinnamon, tarragon, coriander, saffron, ginger.

Especially preferred are animal pests from the order of the mites (Acari), in particular from the families of the gall mites (Eriophyidae), thread-footed mites (Tarsonemidae) and spider mites (Tetranychidae).

Gall Mites (Eriophyidae)

Very especially preferred is the control of the following species from the family of the gall mites (Eriophyidae) in the following crops:

*Aculops lycopersici* in vegetables such as, for example, tomatoes, aubergines, in

*Aculops pelekassi* citrus such as, for example, oranges, grapefruits, tangerines

*Aculus schlechtendali* in pome fruit such as, for example, apples, in stone fruit

*Aculus fokeui*, such as, for example, quetsch, peaches

*Aculus berochensis*

*Aculus conutus*

*Aceria sheldoni* in citrus such as, for example oranges, clementines, limes, in

*Aceria tulipai* vegetables such as, for example, onions, cereals such as, for example, wheat

*Epitrimerus pyri* in pome fruit such as, for example, pears, in grapevines

*Epitrimerus vitis*

*Eriophyes avellanae* in nuts, such as, for example, hazelnuts, in conifers, in

*Eriophyes guerreronis* tropical crops such as, for example, coconuts, lychees, in

*Eriophyes litchii* pome fruit such as, for example pears, in soft fruits such as,

*Eriophyes piri* for example, currants, in tea, in grapevines

*Eriophyes ribis*

*Eriophyes theae*

*Eriophyes vitis*

*Phyllocoptrutua oleivora* in citrus, such as, for example, oranges, grapefruits, tangerines Thread-Footed Mites (Tarsonemidae)

Very especially preferred is the control of the following species from the family of the thread-footed mites (Tarsonemidae) in the following crops:

*Hemitarsonemus latus* in ornamentals, in cotton, in vegetables such as chillies, bell peppers, tea, conifers Spider Mites (Tetranychidae)

Very especially preferred is the control of the following species from the family of the spider mites (Tetranychidae) in the following crops:

*Brevipalpus lewisi* in citrus such as, for example, oranges, lemons, grapefruits,

*Brevipalpus obovatus* tangerines, in ornamentals, for example Solanaceae, in coffee,

*Brevipalpus oudemansi* in tropical fruit such as, for example, mangos, passion fruit,

*Brevipalpus phoenicis* papayas, in grapevines, in tea, in pome fruit such as, for example apples and pear, in nuts, for example walnuts

*Eotetranychus carpirii* in grapevines, in nuts such as, for example pecan nuts, in

*Eotetranychus willamelti* citrus such as, for example, limes, clementines, grapefruits,

*Eotetranychus hicoriae* pome fruit, for example apples

*Eotetranychus yumensis*

*Panonychus citri* in grapevines, in pome fruit, for example apples, pears, in

*Panonychus ulmi* stone fruit, for example peaches, cherries, quetsch, plums, in citrus such as, for example, oranges, tangerines, grapefruits, limes, in soft fruit such as, for example, currants, in nuts such as, for example, almonds, walnuts

*Tetranychus canadensis* in pome fruit such as, for example, apples, pears, in stone

*Tetranychus urtricae* fruit such as for example, plums, peaches, cherries, in soft

*Tetranychus parcificus* fruit such as, for example, strawberries, gooseberries,

*Tetranychus cinnabarinus* raspberries, in vegetables such as, for example, tomatoes,

*Tetranychus turkestani* cucumber, aubergines, bell pepper, chilies, in ornamentals

*Tetranychus viennensis* such as, for example, orchids, flower maple, in conifers, in

*Tetranychus kanzawai* woody species, in grapevines, in nuts such as, for example, almonds, pistachios, in cotton, in tea, in hops

*Oligonychus coffeae* in coffee, in maize, in tropical fruits such as, for example

*Oligonychus ilicis* avocados, persimmon, in stone fruit such as, for example

*Oligonychus mexicanus* plums, in grapevines

*Oligonychus persea*

*Oligonychus punicae*

All plant and plant parts may be treated in accordance with the invention. In the present context, plants are understood as meaning all plants and plant populations, such as desired and undesired wild plants or crop plants (including naturally occurring crop plants). Crop plants may be plants which can be obtained by traditional breeding and optimization methods or by biotechnological methods and genetic engineering methods or combinations of these methods, including the transgenic plants and including the plant varieties capable or not of being protected by Plant Breeders' Rights. Plant parts are understood as meaning all aerial and subterranean parts and organs of the plants, such as shoot, leaf, flower and root, examples which may be mentioned being leaves, needles, stems, stalks, flowers, fruiting bodies, fruits and seeds, and also roots, tubers and rhizomes. The plant parts also include harvested product and vegetative and generative propagation material, for example cuttings, tubers, rhizomes, slips and seeds.

The treatment according to the invention of the plants and plant parts with the active substance combinations is carried out directly or by acting on their environment, habitat or store, using customary treatment methods, for example by dipping, spraying, vaporizing, misting, scattering, painting on, injecting and, in the case of propagation material, in particular seeds, furthermore by applying one or more coats.

As already mentioned above, all plants and their parts can be treated in accordance with the invention. In a preferred embodiment, plant species and plant varieties which are found in the wild or are obtained by traditional biological breeding methods, such as hybridization or protoplast fusion, and parts of the former are treated. In a further preferred embodiment, transgenic plants and plant varieties which have been obtained by recombinant methods, if appropriate in combination with traditional methods (genetically modified organisms) and their parts are treated. The term "parts" or "parts of plants" or "plant parts" has been illustrated above.

Particularly preferably, plants of the plant cultivars which are in each case commercially available or in use are treated according to the invention. Plant cultivars are understood as meaning plants with new properties ("traits") which have been obtained by conventional cultivation, by mutagenesis or else by recombinant DNA techniques. These may be cultivars, biotypes or genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or extensions of the activity spectrum and/or an increase in the activity of the substances and compositions that can be used according to the invention, better plant growth, increased tolerance to high or low temperatures, increased tolerance to drought or to water or soil salinity, increased flowering performance, easier harvesting, accelerated maturation, higher harvest yields, better quality and/or a higher nutritional value of the harvested products, better storage stability and/or processability of the harvested products which exceed the effects which were actually to be expected are possible.

The preferred transgenic plants or plant cultivars (i.e. those obtained by genetic engineering) which are to be treated according to the invention include all plants which, as a result of the recombinant modification, received genetic material which imparted particularly advantageous useful properties ("traits") to these plants. Examples of such properties are better plant growth, increased tolerance to high or low temperatures, increased tolerance to drought or to water or soil salinity, increased flowering performance, easier harvesting, accelerated maturation, higher yields, better quality and/or a higher nutritional value of the harvested products, better storage stability and/or processability of the harvested products.

Further and particularly emphasized examples of such properties are a better defense of the plants against animal and microbial pests, such as against insects, mites, phytopathogenic fungi, bacteria and/or viruses, and also increased tolerance of the plants to certain herbicidally active substances. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defense of the plants against insects, arachnids, nematodes, slugs and snails as a result of toxins formed in the plants, in particular those formed in the plants by the genetic material from Bacillus thuringiensis (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits which are also particularly emphasized are the increased defense of plants against fungi, bacteria and viruses by systemic acquired resistance (SAR), systemin, phytoalexins, elicitors and resistance genes and the correspondingly expressed proteins and toxins. Traits that are furthermore particularly emphasized are the increased tolerance of the plants to certain herbicidally active substances, for example imidazolinones, sulfonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), Knock-Out® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinothricin, for example oilseed rape), IMI® (tolerance to imidazolinones) and STS® (tolerance to sulfonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars having these genetic traits or genetic traits still to be developed, which cultivars will be developed and/or marketed in the future.

The active substance combinations can be converted into the customary formulations, such as solutions, emulsions, wettable powders, suspensions, powders, dusts, pastes, soluble powders, granules, suspension emulsion concentrates, natural and synthetic materials impregnated with active substance, and microencapsulations in polymeric substances.

These formulations are prepared in the known manner, for example by mixing the active substance with extenders, that is to say liquid solvents and/or solid carriers, optionally with the use of surface-active agents, i.e. emulsifiers and/or dispersants and/or foam formers.

Examples of suitable extenders are water, polar and unpolar organic chemical liquids, for example from the classes of the aromatic and nonaromatic hydrocarbons (such as paraffins, alkylbenzenes, alkylnaphthalenes, chlorobenzenes), of the alcohols and polyols (which may optionally also be substituted, etherified and/or esterified), of the ketones (such as acetone, cyclohexanone), of the esters (also fats and oils) and (poly)ethers, of the unsubstituted or substituted amines, amides, lactams (such as N-alkylpyrrolidones) and lactones, of the sulfones and sulfoxides (such as dimethyl sulfoxide).

If water is used as the extender, it is possible to use for example also organic solvents as cosolvents. Liquid solvents which are suitable in the main are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and water.

Solid carriers which are suitable are:
for example ammonium salts and ground natural minerals such as kaolins, clays, talc, chalk, quartz, attapulgite, montmorillonite or diatomaceous earth, and ground synthetic minerals such as highly disperse silica, alumina and silicates, suitable solid carriers for granules are: for example crushed and fractionated natural rocks such as calcite, marmor, pumice, sepiolite, dolomite, and synthetic granules of inorganic and organic meals, and granules of organic material such as sawdust, coconut shells, maize cobs and tobacco stalks; emulsifiers and/or foam formers which are suitable are: for example nonionic and anionic emulsifiers such as polyoxyethylene fatty acid esters, polyoxyethylene fatty alcohol ethers, for example alkylaryl polyglycol ethers, alkylsulfonates, alkyl sulfates, arylsulfonates and protein hydrolysates; examples of dispersants are: for example lignin-sulfite waste liquors and methylcellulose.

Adhesives such as carboxymethylcellulose, natural and synthetic polymers in the form of powders, granules or latices, such as gum arabic, polyvinyl alcohol, polyvinyl acetate, and natural phospholipids, such as cephalins and lecithins, and synthetic phospholipids may be used in the formulations. Further additives may be mineral and vegetable oils.

It is possible to use colorants such as inorganic pigments, for example iron oxide, titanium oxide, Persian blue, and organic dyestuffs such as alizarin, azo and metal phthalocyanine dyestuffs, and trace nutrients such as salts of iron, manganese, boron, copper, cobalt, molybdenum and zinc.

In general, the formulations contain between 0.1 and 95% by weight of active substance, preferably between 0.5 and 90% and, additionally, preferably extenders and/or surface-active agents.

The active substance content of the use forms prepared from the commercially available formulations may vary within wide ranges. The active substance concentration of the use forms may be from 0.0000001 up to 95% by weight of active substance, preferably between 0.0001 and 1% by weight.

Application is effected in a customary manner adapted to suit the use forms.

According to the invention, the abovementioned plants can be treated especially advantageously with the active substance combinations according to the invention. The preferred ranges stated for the mixtures hereinabove also apply to the treatment of these plants. The plant treatment with the mixtures specifically mentioned in the present text may be particularly emphasized.

The good insecticidal activity of the active substance combinations can be seen from the examples which follow. While the individual active substances have weaknesses in their activity, the combinations display an activity which exceeds a simple sum of activities.

A synergistic effect in insecticides is always present when the activity of the active substance combinations exceeds the sum of the activities of the active substances when applied individually.

The activity which can be expected for a given combination of two active substances can be calculated as defined by S. R. Colby, Weeds 15 (1967), 20-22) as follows:
if
X is the degree of destruction expressed in % of the untreated control when employing the active substance A at an application rate of m g/ha or a concentration of m ppm,
Y is the degree of destruction expressed in % of the untreated control when employing the active substance B at an application rate of n g/ha or a concentration of n ppm and
E is the degree of destruction expressed in % of the untreated control when employing the active substances A and B at application rates of m and n g/ha or a concentration of m and n ppm,
then $$E = X + Y - \frac{X \cdot Y}{100}$$

If the actual degree of insecticidal destruction is greater than calculated, then the destruction of the combination is super-additive, i.e. a synergistic effect is present. In this case, the actually observed degree of destruction must be greater than the value for the expected degree of destruction in (E) calculated using the abovementioned formula.

Moreover, the activity which can be expected for a given combination of two active substances can also be calculated as follows (cf. Yun-Pei Sun and E. R. Johnson, "Analysis of Joint Action of Insecticides against House Flies", J. Econ. Entomol. 58, 1960, 887ff):

if $LC_{50\ (or\ 95)\ A}$ is the concentration at which 50% (or 95%, respectively) of the animals treated with the active substance A are destroyed, and $LC_{50\ (or\ 95)\ b}$ is the concentration at which 50% (or 95%, respectively) of the animals treated with the active substance B are destroyed, $$\text{the actual tox-index of the mixture} = \frac{LC_{50\ of\ active\ substance\ A}}{LC_{50\ of\ the\ mixture}} \times 100$$

the theoretic tox-index of the mixture = tox-index of active substance $A \times \%$ of $A$ in the mixture + tox-index of active substance $B \times \%$ of $B$ in the mixture, then the cotoxicity coefficient CTC of the mixture =

$$\frac{\text{actual tox-index of the mixture}}{\text{theoretic tox-index of the mixture}} \times 100$$

If the calculated cotoxicity coefficient is greater than 100, a synergistic effect is present.

EXAMPLE A

*Panonychus ulmi* Test

Solvent: 7 parts by weight of dimethylformamide
Emulsifier: 2 parts by weight of alkylaryl polyglycol ether To prepare a suitable preparation of active substance, 1 part by weight of active substance is mixed with the stated amounts of solvent and emulsifier, and the concentrate is diluted with water to the desired concentrations.

Plum cuttings (*Prunus domestica*) which are infected with a mixed population of the fruit tree spider mite (*Panonychus ulmi*) are sprayed with the active substance preparation at the desired concentration.

After the desired period of time, the destruction is determined in %. In this context, 100% means that all spider mites have been destroyed; 0% means that no spider mites have been destroyed.

In this test, a synergistically increased activity in comparison to the active substances when applied individually was shown by the following active substance combination according to the present specification:

TABLE A

| | Plant-injurious mites *Panonychus ulmi* test | | |
|---|---|---|---|
| Active substance | Concentration in ppm | Destruction in % after $2^d$ | |
| Spirodiclofen (I) | 0.8 | 5 | |
| Bifenazate (II) | 0.8 | 10 | |
| | | found* | calc.** |
| Spirodiclofen (I) + Bifenazate (II) (1:1) according to the invention | 0.8 + 0.8 | 80 | 14.5 |
| Fenazaquin (V) | 0.8 | 0 | |
| Spirodiclofen (I) + Fenazaquin (V) (1:1) according to the invention | 0.8 + 0.8 | 40 | 5 |
| Spirodiclofen (I) | 4 | 15 | |
| Abamectin (VI) | 0.16 | 0 | |

TABLE A-continued

| | Plant-injurious mites *Panonychus ulmi* test | |
|---|---|---|
| Active substance | Concentration in ppm | Destruction in % after $2^d$ |
| Spirodiclofen (I) + Abamectin (VI) (25:1) according to the invention | 4 + 0.16 | 60     15 |

*found = found activity
**calc. = activity calculated using Colby's formula

EXAMPLE B

*Tetranychus urticae* Test (OP-Resistant)

Solvent: 7 parts by weight of dimethylformamide
Emulsifier: 2 parts by weight of alkylaryl polyglycol ether To prepare a suitable preparation of active substance, 1 part by weight of active substance is mixed with the stated amounts of solvent and emulsifier, and the concentrate is diluted with water to the desired concentrations.

Cucumbers (*Cucumis sativus*) which are severely infected with the common spider mite (*Tetranychus urticae*) are sprayed with the active substance preparation at the desired concentration.

After the desired period of time, the destruction is determined in %. In this context, 100% means that all spider mites have been destroyed; 0% means that no spider mites have been destroyed.

In this test, a synergistically increased activity in comparison to the active substances when applied individually was shown by the following active substance combination according to the present specification:

TABLE B

| | Plant-injurious mites *Tetranychus urticae* test | | |
|---|---|---|---|
| Active substance | Concentration in ppm | Destruction in % after $6^d$ | |
| Spirodiclofen (I) | 0.16 | 25 | |
| Bifenazate (II) | 0.16 | 15 | |
| | | found* | calc.** |
| Spirodiclofen (I) + Bifenazate (II) (1:1) according to the invention | 0.16 + 0.16 | 60 | 36.25 |
| Spirodiclofen (I) | 0.032 | 15 | |
| Fenazaquin (V) | 0.16 | 0 | |
| Spirodiclofen (I) + Fenazaquin (V) (1:1) according to the invention | 0.032 + 0.16 | 40 | 15 |

*found = found activity
**calc. = activity calculated using Colby's formula

EXAMPLE C

*Panonychus citri* Test

Solvent: 7 parts by weight of dimethylformamide
Emulsifier: 2 parts by weight of alkylaryl polyglycol ether To prepare a suitable preparation of active substance, 1 part by weight of active substance is mixed with the stated amounts of solvent and emulsifier, and the concentrate is diluted with water to the desired concentrations.

Citrus plants (*Citrus limon*) which are infected with a mixed population of the citrus spider mite (*Panonychus citri*) are sprayed with the active substance preparation at the desired concentration.

After the desired period of time, the destruction is determined in %. In this context, 100% means that all spider mites have been destroyed; 0% means that no spider mites have been destroyed.

In this test, a synergistically increased activity in comparison to the active substances when applied individually was shown by the following active substance combination according to the present specification:

TABLE C

| | Plant injurious mites *Panonychus citri* test | |
|---|---|---|
| Active substance | LC 50 in mg/l after $1^d$ | |
| | found* | CTC calc.** |
| Spirodiclofen (I) | 12.2563 | |
| Abamectin (VI) | 1.0054 | |
| Spirodiclofen (I) + Abamectin (VI) (12:1) according to the invention | 1.7803 | 369.97 |
| Pyridaben (IV) | 31.41 | |
| Spirodiclofen (I) + Pyridaben (IV) (1:2) according to the invention | 9.9303 | 295.806 |
| Fenazaquin (V) | 10.2 | |
| Spirodiclofen (I) + Fenazaquin (V) (1:1) according to the invention | 5.7641 | 193.1581 |

CTC = cotoxicity coefficient
*found = found activity
**calc. = activity calculated by the method of Yun-Pei Sun and E. R. Johnson

The invention claimed is:

1. A method of controlling insects or acarids comprising contacting crops or their environment with a compound of the formula (I):

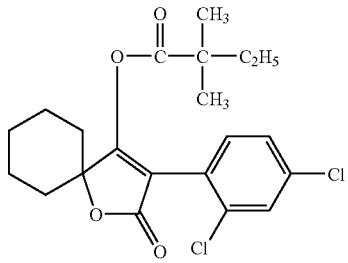

and at least one compound selected from the group consisting of:
bifenazate,
fenpyroximate,
pyridaben,
fenazaquin,
abamectin,
emamectin benzoate,
fenpropathrin and
propargite; and
wherein the crops are stone fruit or citrus.

2. The method according to claim 1, wherein said insects or acarids are from the family of the mites.

3. The method according to claim 1, wherein said insects or acarids are gall mites.

4. The method according to claim 1, wherein said insects or acarids are thread-footed mites.

5. The method according to claim 1, wherein said insects or acarids are spider mites.

6. The method according to claim 1, wherein said insects or acarids are *Panonychus ulmi*.

7. The method according to claim 1, wherein said insects or acarids are *Tetranychus urticae*.

8. The method according to claim 1, wherein said insects or acarids are *Panonychus citri*.

* * * * *